(12) United States Patent
Jiang et al.

US008530064B2

(10) Patent No.: US 8,530,064 B2
(45) Date of Patent: Sep. 10, 2013

(54) MOLD-INHIBITING METHOD AND COMPOSITION COMPRISING DEHYDROACETIC ACID OR SALT THEREOF

(75) Inventors: Xiao Jiang, Emerson, NJ (US); Leigh Walker, East Greenbush, NY (US)

(73) Assignee: Lonza, Inc., Allendale, NJ (US)

( * ) Notice: Subject to any disclaimer, the term of this patent is extended or adjusted under 35 U.S.C. 154(b) by 672 days.

(21) Appl. No.: 12/575,080

(22) Filed: Oct. 7, 2009

(65) Prior Publication Data

US 2010/0105768 A1    Apr. 29, 2010

Related U.S. Application Data

(60) Provisional application No. 61/103,596, filed on Oct. 8, 2008.

(51) Int. Cl.
*C11D 3/48* (2006.01)

(52) U.S. Cl.
USPC ............. 428/703; 428/537.5; 428/537.7; 156/39; 156/44; 156/45; 162/161; 510/199; 510/383; 510/384; 510/391

(58) Field of Classification Search
USPC ............. 428/537.5, 537.7, 703; 156/39, 156/44, 45; 162/161; 510/199, 382, 384, 510/391
See application file for complete search history.

(56) References Cited

U.S. PATENT DOCUMENTS

| | | | | |
|---|---|---|---|---|
| 3,918,981 A | * | 11/1975 | Long | 106/16 |
| 4,303,668 A | * | 12/1981 | Hasegawa et al. | 514/646 |
| 4,323,565 A | * | 4/1982 | Hasegawa et al. | 514/223.8 |
| 4,548,676 A | * | 10/1985 | Johnstone et al. | 162/135 |
| 5,186,947 A | * | 2/1993 | Goettsche et al. | 424/638 |
| 5,783,626 A | * | 7/1998 | Taylor et al. | 524/555 |
| 2002/0090462 A1 | * | 7/2002 | Obie | 427/415 |
| 2006/0086284 A1 | * | 4/2006 | Zhang et al. | 106/15.05 |
| 2006/0288904 A1 | * | 12/2006 | Leach et al. | 106/15.05 |
| 2009/0162410 A1 | * | 6/2009 | Zhang et al. | 424/409 |

FOREIGN PATENT DOCUMENTS

| | | | |
|---|---|---|---|
| WO | 00/59696 | * | 10/2000 |
| WO | 0059696 | | 10/2000 |
| WO | 02069710 A1 | | 9/2002 |

* cited by examiner

*Primary Examiner* — Charles Boyer

(74) *Attorney, Agent, or Firm* — Hoffman & Baron, LLP

(57) ABSTRACT

Disclosed is a method for inhibiting the growth of mold on building materials by application onto and/or incorporation into the building material of a mold-inhibiting composition comprising dehydroacetic acid or a salt thereof and, optionally, an additional fungicidal agent such as a quaternary ammonium compound. A preferred application of the method is the inhibition of mold growth on plasterboard (drywall).

8 Claims, 2 Drawing Sheets

MOLD-INHIBITING METHOD AND COMPOSITION COMPRISING DEHYDROACETIC ACID OR SALT THEREOF

CROSS-REFERENCE TO RELATED APPLICATION

This application claim the benefit of priority from U.S. Provisional Patent Application No. 61/103,596 filed Oct. 8, 2008, the disclosure of which is incorporated herein by reference.

BACKGROUND OF THE INVENTION

The invention relates to a method for inhibiting or preventing the growth of mold, mildew and fungi on building or construction materials such as wood and drywall (also known as plasterboard).

Mold, mildew and bacteria are the leading biological pollutants generated in a home. According to the Centers for Disease Control and Prevention (CDC), mold is everywhere. It can be found both indoors and outdoors. Outdoors, mold is commonly found in shady and damp areas. Indoors, it can be found where humidity and moisture levels are high, such as in basements, kitchens, bathrooms, and on ceilings and wall interiors where water from leaky pipes, roofs or windows can accumulate. Mold and mildew have been found on different materials such as cellulose based materials (solid wood, wood composites, wood polymer composites, paper, etc.), plastics, gypsum boards, ceiling tiles, vinyl siding, roofs, etc. Mold can cause different types of problems, from unpleasant odor, discoloration problems, deterioration of building materials to serious health problems. While most molds pose no threat to humans, the CDC warns that certain molds can produce allergic symptoms and the concerns are increasing. Therefore, it is important to prevent mold and mildew growth.

There is an ongoing need for a cost-effective, broad spectrum antimicrobial agent that can be added to building materials which are subject to mold/mildew attack. It has been recognized a long time ago that the biodeterioration of plastics is a problem, especially with plasticized polyvinyl chloride (PVC). Cellulose-based materials can serve as microbial nutrients and therefore are susceptible to mold/mildew attack. It is also a known fact that even wood that has been pressure treated with conventional wood preservatives such as ACQ (copper oxide/quat), copper azole, or CCA (chromated copper arsenate) could be subject to mold/mildew growth. Moreover, preservatives containing copper, chromium and in particular arsenic are objectionable from a toxicological and environmental point of view. It was therefore an object of the present invention to provide a method for inhibiting or preventing mold growth on building materials without using heavy metal compounds.

SUMMARY OF THE INVENTION

Applicants have found that either dehydroacetic acid (DHA) or salts of DHA, alone or in conjunction with co-biocides is an effective anti-mold/anti-mildew system without compromising the structural integrity of the treated materials such as gypsum board, wood, wood composites, wood polymer composites, etc. It can be either incorporated into or applied onto the materials to reduce or eliminate the growth of mold/mildew. Unlike many other fungicides which are not water-soluble, DHA based anti-mold/anti-mildew systems are water soluble, efficacious, and cost-effective.

According to the invention, mold growth on a building material is inhibited or prevented by application onto and/or incorporation into said building material of a mold-inhibiting composition comprising dehydroacetic acid or a salt thereof.

In a preferred embodiment, the mold-inhibiting composition further comprises at least one additional fungicidal agent and/or one additional fungicidity-enhancing agents such as amine oxides and amines.

More preferably, the at least one additional fungicidal agent is a fungicidal quaternary ammonium compound. Suitable fungicidal quaternary ammonium compounds include, but are not limited to, those having the formula $R^1R^2R^3R^4N^+ X^-$, where $R^1$, $R^2$, $R^3$, and $R^4$ independently are linear, branched, cyclic or any combination thereof saturated or unsaturated groups and $X^-$ is an anion. The sum of the number of carbon atoms in $R^1$, $R^2$, $R^3$, and $R^4$ broadly ranges from about 10 to 50. $R^1$, $R^2$, $R^3$, and $R^4$ may be alkyl, alkenyl, alkynyl, cycloalkyl, aryl, or any combination of any of the foregoing. $X^-$ may be chloride, bromide, iodide, borate, carbonate, bicarbonate, nitrite, dehydroacetate, or a carboxylate such as acetate, laurate or stearate. Suitable carboxylate and borate anions include, but are not limited to, those disclosed in U.S. Pat. No. 5,641,726, which is hereby incorporated by reference.

Suitable amine oxides include, but are not limited to a trialiphatic substituted amine oxide, an N-alkylated cyclic amine oxide, a dialkylpiperazine di-N-oxide, an alkyldi-(hydroxylated oxyalkyl)amine oxide, a dialkylbenzylamine oxide, a [3-(N-fatty acylamino)propyl]dimethylamine oxide, a diamine oxide, a triamine oxide, or any combination of any of the foregoing.

Suitable amines include, but are not limited to those having the formula $R^5R^6R^7N$, where $R^5$, $R^6$, and $R^7$ independently are linear, branched, cyclic or any combination thereof saturated or unsaturated groups. The sum of the number of carbon atoms in $R^5$, $R^6$, and $R^7$ broadly ranges from about 10 to 50. $R^5$, $R^6$, and $R^7$ may be alkyl, alkenyl, alkynyl, cycloalkyl, aryl, or any combination of any of the foregoing.

Even more preferred additional fungicidal agents fungicidal quaternary ammonium compounds are the di($C_{8-18}$ alkyl)dimethylammonium compounds.

Particularly preferred di($C_{8-18}$ alkyl)dimethylammonium compounds are selected from di($C_{8-18}$ alkyl)dimethylammonium carbonates, di($C_{8-18}$ alkyl)dimethylammonium bicarbonates and mixtures thereof, the most preferred di($C_{8-18}$ alkyl)dimethylammonium compound being didecyldimethylammonium carbonate/bicarbonate.

The method of the invention can be applied to any building material that is prone to mold attack, in particular materials such as wood, wood composites such as fiberboard, hardboard, particle board, wafer board, wood-polymer composites, gypsum and plasterboard (drywall).

In a preferred embodiment the mold-inhibiting composition is incorporated in the building material in an amount sufficient to obtain a concentration of dehydroacetic acid or salt thereof in the building material of between 500 ppm and 10,000 ppm by weight.

In an especially preferred embodiment the building material is paper-lined gypsum (plasterboard, drywall) and the mold-inhibiting composition is applied to the paper lining in an amount sufficient to obtain a concentration of dehydroacetic acid or salt thereof in the paper lining of between 500 ppm and 10,000 ppm by weight. In addition to its application to the paper lining the mold-inhibiting composition may also be incorporated into the gypsum core, as described above.

Another object of the invention is a mold inhibiting composition comprising (a) dehydroacetic acid or a salt thereof and (b) at least one component selected from fungicidal quaternary ammonium compounds, and/or from the fungicidity-enhancing agents such as amine oxides and amines, in a weight ratio (a):(b) in the range of from 1:20 to 10:1.

In a preferred embodiment component (b) of the mold-inhibiting composition comprises a fungicidal quaternary ammonium compound selected from di($C_{8-18}$ alkyl)dimethyl ammonium carbonates, di($C_{8-18}$ alkyl)dimethylammonium bicarbonates, and mixtures thereof.

In a still more preferred embodiment, component (b) comprises didecyldimethylammonium carbonate/bicarbonate.

Still another object of the invention is the use of a mold-inhibiting composition as described above for the application onto and/or incorporation into a building material selected from wood, wood composites such as fiberboard, hardboard, particle board, wafer board, wood-polymer composites, gypsum and plasterboard (drywall).

In a particularly preferred embodiment of said use, the building material is paper-lined gypsum (plasterboard, drywall) and the mold-inhibiting composition is applied to the paper lining and, optionally, incorporated into the gypsum.

Yet another object of the invention is a mold-inhibited building material treated with a mold-inhibiting composition as described above.

In a particularly preferred embodiment said mold-inhibited building material is paper-lined gypsum (plasterboard, drywall) and the mold-inhibiting composition is applied to the paper lining and, optionally, incorporated into the gypsum.

DETAILED DESCRIPTION OF THE INVENTION

Examples

Figure 1:
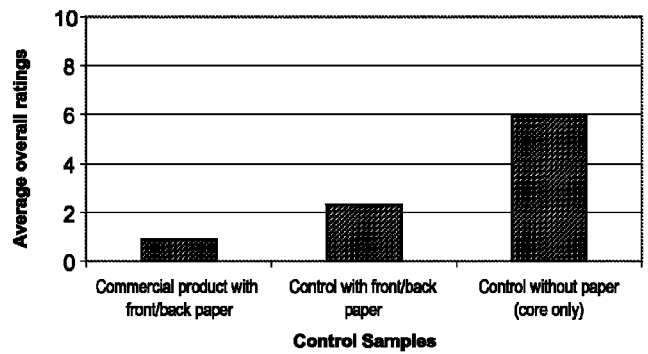
FIG. 1 depicts the results of control experiments with commercially available and laboratory-made wallboard and with a laboratory-made gypsum board without paper liners after the ASTM D3273 test (4 weeks exposure) as described in Example 3.

The following non-limiting examples will illustrate the invention.

Unless otherwise specified, all concentrations in percent or ppm are by weight and all pressures are relative to atmospheric pressure.

Example 1

Air-dried southern yellow pine wood blocks (8.9×6.35×3.8 $cm^3$) were pressure treated (initial vacuum to −90 kPa, kept at this vacuum condition for 20 min; injected treating solution and introduced air pressure to the treating cylinder to 400 kPa, and kept at this pressure condition for 20 min) with the following prepared formulations:

(1) Water
(2) 0.33% AC (Monoethanolamine copper carbonate solution)
(3) 0.5% ACQ-D[1]
(4) 0.5% ACQ-D+0.2% Barlox® 12[2]/DHA

[1] ACQ-D contains 66.7% copper oxide and 33.3% didecyldimethylammonium chloride

[2] Barlox® 12 is N-cocoalkyl-N,N-dimethylamine oxide

The treated wood blocks were placed in plastic sandwich bags immediately after treatment, and the bags were sealed to maintain the moisture content.

Visual observation of mold growth on the wood blocks was recorded periodically using the following rating system. The samples were evaluated weekly for the first two weeks, and then evaluated every two weeks for the rest of the test. At week 8, fresh spore suspensions of *A. niger* and *P. citrinum* were sprayed on the surface of wood blocks and then the inoculated wood blocks were placed in plastic bags and sealed. The test was completed at 12 weeks.

0: No mold growth
1: Slight mold growth (<5% mold coverage)
2: Medium mold growth (6-25% mold coverage)
3: Heavy mold growth (26-50% mold coverage)
4: Severe mold growth (>50% mold coverage)

The test results are reported in Table 1 using the designed rating system. The water treated control showed heavy mold growth in the first week of the test, and AC treatment showed slight mold growth at week 6. The other two treatment remained free of molds within 8 weeks. At the $8^{th}$ week of the test, mold spore suspensions of *A. niger* and *P. citrinum* were spayed on the surface of all test samples to create a more aggressive mildew condition. Under the severe mildew test environment, at the end of the test, wood treated with 0.5% ACQ-D showed moderate mold growth, but wood treated with 0.5% ACQ-D with the addition of 0.166% Barlox® 12 and 0.033% DHA was mold free.

TABLE 1

| | Visual evaluation | | | | | | |
|---|---|---|---|---|---|---|---|
| Treatments | Week 1 | Week 2 | Week 4 | Week 6 | Week 8* | Week 10 | Week 12 |
| Water | 3 | 4 | 4 | 4 | 4 | 4 | 4 |
| 0.33% AC | 0 | 0 | 0 | 1 | 2 | 3 | 3 |
| 0.5% ACQ-D | 0 | 0 | 0 | 0 | 0 | 1 | 2 |
| 0.5% ACQ-D + 0.166% Barlox ® 12 + 0.033% DHA | 0 | 0 | 0 | 0 | 0 | 0 | 0 |

*Mold spore suspensions were sprayed on the surface of wood blocks.

Example 2

Gypsum cuboids (30×40×25 $mm^3$) were made with the addition of the following formulations:

Sodium dehydroacetic acid (Na-DHA): 2500 ppm and 5000 ppm.
Carboquat® 250T[3]: 2500 ppm and 5000 ppm.
Carboquat® 250T/DHA 10:4 (wt./wt.): 2500 ppm and 5000 ppm.

[3] Carboquat® 250T is an essentially aqueous solution containing approx. 50% of a mixture of carbonate and bicarbonate of didecyldimethylammonium. Carboquat® 250T is available from Lonza Inc., Allendale N.J.

Glass containers with Sabouraud's Dextrose Agar (SDA) on the bottom were prepared. Freshly-made spore suspensions of *A. niger* and *P. citrinum* were spread on the surface of SDA. The gypsum cuboids were air-dried and then placed on the top of the inoculated SDA. The containers were covered by aluminum foil and placed in an incubator with pre-set temperature of 26° C. and relative humidity of 70%. The test was completed at 4 weeks. Visual observation of mold growth on the gypsum cuboids was recorded weekly using the same rating system as in Example 1.

The test results were recorded in Table 2 using the designed rating system.

TABLE 2

|  | Visual evaluation | | | |
| --- | --- | --- | --- | --- |
| Treatments | Week 1 | Week 2 | Week 3 | Week 4 |
| Untreated control | 3 | 4 | 4 | 4 |
| Na-DHA (2500 ppm) | 0 | 2 | 3 | 3 |
| Na-DHA (5000 ppm) | 0 | 0 | 0 | 0 |
| Carboquat ® 250T (2500 ppm) | 1 | 2 | 2 | 3 |
| Carboquat ® 250T (5000 ppm) | 0 | 0 | 0 | 0 |
| Carboquat ® 250T/DHA (2500 ppm) | 0 | 1 | 1 | 1 |
| Carboquat ® 250T/DHA (5000 ppm) | 0 | 0 | 0 | 0 |

The untreated control demonstrated heavy mold growth starting at week one of the test. Na-DHA performed similarly to Carboquat® 250T. The combination of DHA and Carboquat® 250T showed slight mold growth at the level of 2500 ppm. At the high concentration level (5000 ppm), there was no mold growth on the samples treated with either Na-DHA alone, Carboquat® 250T alone, or the combination of the two.

Example 3

The mold resistance of gypsum board samples was evaluated using the test ASTM D3273 method.
Methodology:
Preparation of Gypsum Board Samples for ASTM D3273 Test:

A gypsum slurry was prepared by mixing 722 g of stucco plaster (calcium sulfate hemihydrate) with 463 g of water. The mixture was poured into a rectangular metal tray fully covered with aluminum foil, with the back paper placed on the bottom of the tray. Then the front paper was placed on the top of the slurry. After 9 min, the tray containing the gypsum slurry with front and back paper was placed in an oven with a pre-set temperature of 245° C. for 30 minutes.

For the Carboquat® 250T or Carboquat® 250T/DHA treated gypsum, each formulation was prepared by adding 1000 ppm of active ingredient(s) to the 463 g of water used for preparing the gypsum slurry. The front paper was treated with the test formulations by brushing. The concentration of active ingredient(s) in the front paper was determined by the concentration of treating solution used for brushing and the weight difference before and after brushing and was calculated using the following formula:

concn. in paper=(wt. of wet paper after brushing−wt. of dry paper before brushing)×concn. of treating solution/wt. of paper before brushing The back paper was not treated.

The prepared gypsum board was cut into 7.6×10.2 cm$^2$ rectangles for the ASTM D3273 test. The test was performed using 3 replicates for each treatment.
ASTM D3273 Procedure:

The ASTM D3273 test was conducted by The MicroStar-Lab Ltd. (Crystal Lake, Ill., USA). Three weeks prior to testing, fresh soil was seeded with spores of *Aspergillus niger* ATCC 6275, *Penicillium citrinum* ATCC 9849, and *Aureobasidium pullulans* ATCC 9348. The test molds were allowed to grow in a humidified chamber at 98-99% relative humidity and 30° C. After 2 weeks, PDA (potato dextrose agar) plates were placed in the chamber for 30 minutes to determine whether fungal spores were being produced by the fungi seeded into the soil. After confirmation of fungal sporulation, the gypsum board samples were hung in the chamber. Untreated commercial gypsum board pieces were also hung in the chamber as additional controls. The samples were inspected weekly for fungal growth and rated according to the ASTM D3273 grading scale shown below.

| Rating | Definition |
| --- | --- |
| 10 | No growth |
| 9 | 90% clear (≦10% of surface covered with growth) |
| 8 | 80% clear (20% of surface covered with growth) |
| 7 | 70% clear (30% of surface covered with growth) |
| 6 | 60% clear (40% of surface covered with growth) |
| 5 | 50% clear (50% of surface covered with growth) |
| 4 | 40% clear (60% of surface covered with growth) |
| 3 | 30% clear (70% of surface covered with growth) |
| 2 | 20% clear (80% of surface covered with growth) |
| 1 | 10% clear (90% of surface covered with growth) |
| 0 | 0% clear (100% of surface covered with growth) |

Test Results and Discussion

Three types of controls were used in this test: a commercial untreated control with front/back paper (purchased locally by MicroStarLab), a laboratory-made untreated control with front and back paper, and a laboratory-made core control without paper liners. The core control with no paper on the surfaces had significantly less mold attack than the controls with front and back paper (FIG. 1). This suggests that the paper on the gypsum board is the primary nutrient source for molds.

Figure 2:
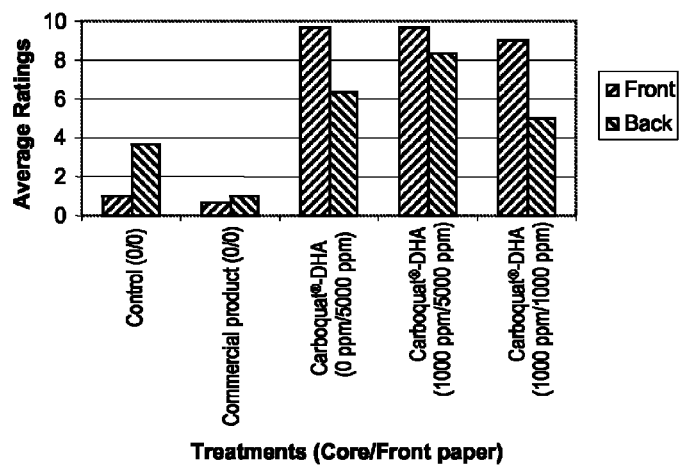
FIG. 2 depicts the results of tests with commercially available and laboratory-made wallboard treated with various amounts of dehydroacetic acid and/or didecyldimethylammonium carbonate/bicarbonate, as described in Example 3 below. Depicted are the average ratings of front side and back side at week 4.

In all test samples, the back paper was not treated. Only the front paper and/or core material was treated. Therefore, it is not surprising that better efficacy against molds was generally found for the front side of the samples, as illustrated in FIG. 2.

Figure 3:
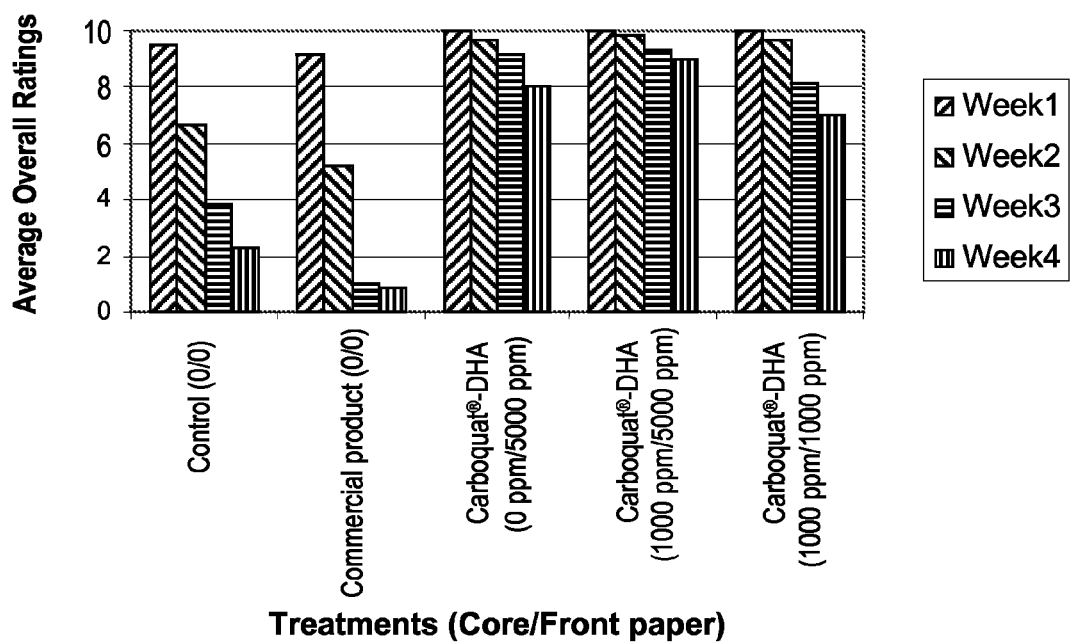
FIG. 3 depicts the results of tests with commercially available and laboratory-made wallboard treated with various amounts of dehydroacetic acid and/or didecyldimethylammonium carbonate/bicarbonate, as described in Example 3 below. Depicted are the average overall ratings at weeks 1 to 4.

For the core treatment, 1000 ppm of active ingredient(s) was applied. Two concentration levels of 1000 ppm and 5000 ppm of active ingredient(s) were used to treat the front paper. As can be seen in FIG. 3, Carboquat®-DHA showed strong efficacy performance against molds at all treatment levels. The best result was generated from the treatment of Carboquat®-DHA with 1000 ppm in the core and 5000 ppm on the front paper.

Example 4

Air-dried southern yellow pine wood stakes (33×5.1×2.5 cm$^3$) were pressure treated (initial vacuum to −90 kPa, kept at this vacuum condition for 20 min; injected treating solution and introduced air pressure to the treating cylinder to 400 kPa, and kept at this pressure condition for 20 min) with the formulations listed below. All the treating solutions were applied in wood with 1% of total solids. The treated samples were placed outdoors and visual observation of mold/mildew growth on and brightness of the wood stakes was recorded annually over a period of two years.
Tested Formulations:
1.0% total solid of Carboquat® 250T/Barlox® 12 (1:1)
1.0% total solid of Carboquat® 250T/Barlox® 12/DHA (1:1: 0.2)
1.0% total solid of Carboquat® 250T
1.0% total solid of Carboquat® 250T/DHA (1:0.1)

1.0% total solid of Barlox® 1612[4]
1.0% total solid of Barlox® 1612/DHA (1:0.1)
1.0% total solid of Barlox® 12
1.0% total solid of Barlox® 12/DHA (1:0.1)
1.0% total solid of Carboquat® 250T/Barlene® 16S[5] (1:1)
1.0% total solid of Carboquat® 250T/Barlene® 16S and DHA (1:1:0.2)

[4] Barlox® 1612 is the mixture of Barlox® 16S (N,N-dimethylhexadecylamine oxide) and Barlox® 12, available from from Lonza Inc., Allendale N.J.
[5] Barlene® 16S is N,N-dimethylhexadecylamine, available from from Lonza Inc., Allendale N.J.

The Rating System was Designed as Follows:
0: Clean and bright
1: Slight mold/mildew growth and darkness
2: Moderate mold/mildew growth and darkness
3: Heavy mold/mildew growth and darkness The inspection results are listed in Table 3. It was confirmed that wood treated with the formulations containing DHA showed enhanced resistance to mold/mildew growth, and the wood containing DHA remained cleaner and brighter.

TABLE 3

| Treatment (Formula Components & Ratios) | Year 1 Front | Year 1 Back | Year 2 Front | Year 2 Back |
|---|---|---|---|---|
| Water (control) | 3 | 3 | 3 | 3 |
| 1% total solid of Carboquat ® 250T/Barlox ® 12 (1:1) | 2 | 3 | 2 | 3 |
| 1% total solid of Carboquat ® 250T/Barlox ® 12/DHA (1:1:0.2) | 0 | 0 | 0 | 1 |
| 1% total solid of Carboquat ® 250T alone | 0 | 3 | 1 | 3 |
| 1% total solid of Carboquat ® 250T/DHA (1:0.1) | 0 | 0 | 0 | 0 |
| 1% total solid of Barlox ® 1612 | 1 | 2 | 2 | 2 |
| 1% total solid of Barlox ® 1612/DHA (1:0.1) | 0 | 0 | 1 | 0 |
| 1% total solid of Barlox ® 12 | 2 | 2 | 2 | 3 |
| 1% total solid of Barlox ® 12/DHA (1:0.1) | 0 | 0 | 2 | 1 |
| 1% total solid of Carboquat ® 250T/Barlene ® 16S (1:1) | 2 | 2 | 3 | 3 |
| 1% total solid of Carboquat ® 250T/Barlene ® 16S/DHA (1:1:0.2) | 0 | 0 | 1 | 0 |

Example 5

Fresh cut white pine blocks (7.6×6.35×3.8 cm³) were dipped in the prepared test formulation for one minute. The individual dipped wood block was placed in a plastic sandwich bag and the plastic bag was sealed to retain the moisture of the test wood blocks. No mold or stain fungi were inoculated on the test blocks. The test blocks were evaluated by visual observation for mold and stain growth and rated using the same system listed in Example 1. The test was completed in 8 weeks.

The mold/stain ratings are listed in Table 4. As can be seen from the data, the untreated and water treated control demonstrated heavy or severe mold/stain growth since week 2. Na-DHA at 1% showed strong efficacy against mold/stain fungi. Another two organic acid salts of Na-Sorbate and Na-Benzoate showed no efficacy. The addition of DHA in the formulation of Carboquat®/Barlox® 12 demonstrated strong efficacy and protected the samples effectively from mold/stain growth.

TABLE 4

| | Visual evaluation | | | | | | |
|---|---|---|---|---|---|---|---|
| Treatments | Week 1 | Week 2 | Week 3 | Week 4 | Week 5 | Week 6 | Week 8 |
| Untreated | 1 | 4 | 4 | 4 | 4 | 4 | 4 |
| Water | 1 | 4 | 4 | 4 | 4 | 4 | 4 |
| 1% Na-DHA | 0 | 0 | 0 | 0 | 1 | 1 | 2 |
| 1% Na-Sorbate | 2 | 4 | 4 | 4 | 4 | 4 | 4 |
| 1% Na-Benzoate | 2 | 4 | 4 | 4 | 4 | 4 | 4 |
| 0.5% Carboquat ® 250T/0.5% Barlox ® 12 | 0 | 1 | 2 | 3 | 4 | 4 | 4 |
| 0.5% Carboquat ® 250T/0.5% Barlox ® 12/1000 ppm DHA | 0 | 0 | 0 | 0 | 0 | 0 | 1 |

Thus, while applicants have described what are presently believed to be the preferred embodiments of the invention, other and further changes and modifications will be appreciated by those skilled in art, and it is intended to include all such changes and modifications as come within the true scope of the invention as outlined in the appended claims.

The invention claimed is:

1. A method for inhibiting mold growth on paper-lined gypsum, said method comprising the application onto and/or incorporation into said paper-lined gypsum of a mold-inhibiting composition comprising:
   i) dehydroacetic acid or a salt thereof, and
   ii) at least one additional fungicidal agent, wherein the at least one additional fungicidal agent is a di($C_{8-18}$ alkyl)dimethylammonium compound.

2. The method of claim 1, wherein the di($C_{8-18}$ alkyl)dimethylammonium compound is selected from di($C_{8-18}$ alkyl) dimethylammonium carbonates, di($C_{8-18}$ alkyl)dimethylammonium bicarbonates, and mixtures thereof.

3. The method of claim 2, wherein the di($C_{8-18}$ alkyl)dimethylammonium compound is didecyldimethylammonium carbonate/bicarbonate.

4. The method of claim 1, wherein the mold-inhibiting composition is applied to the paper lining in an amount sufficient to obtain a concentration of dehydroacetic acid or salt thereof in the paper lining of between 500 ppm and 10,000 ppm by weight.

5. A method of inhibiting mold growth in a paper-lined gypsum comprising the application onto and/or incorporation into a paper-lined gypsum a mold-inhibiting composition comprising, a (a) dehydroacetic acid or a salt thereof and (b) an additional fungicidal agent in a weight ratio (a):(b) in the range of from 1:20 to 10:1, wherein the at least one additional fungicidal agent is a di($C_{8-18}$ alkyl)dimethylammonium compound.

6. The method of claim 5 wherein the mold-inhibiting composition is applied to the paper lining and, optionally, incorporated into the gypsum.

7. The method for inhibiting mold growth according to claim 1 wherein said mold-inhibiting composition further comprises a fungicidity-enhancing agent selected from amine oxides and amines.

8. The method according to claim 5 wherein said mold-inhibiting composition further comprises a fungicidity-enhancing agent selected from amine oxides and amines.

* * * * *